United States Patent [19]
Miyazawa et al.

[11] Patent Number: 6,117,360
[45] Date of Patent: *Sep. 12, 2000

[54] LIQUID CRYSTAL COMPOSITION AND LIQUID CRYSTAL DISPLAY DEVICE

[75] Inventors: Kazutoshi Miyazawa; Shuichi Matsui; Tomoyuki Kondo; Takashi Kato; Yasuko Sekiguchi; Etsuo Nakagawa, all of Chiba, Japan

[73] Assignee: Chisso Corporation, Osaka-Fu, Japan

[*] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/698,451

[22] Filed: Aug. 15, 1996

[30] Foreign Application Priority Data

Sep. 11, 1995 [JP] Japan ................................. 7-258185

[51] Int. Cl.[7] .......................... C09K 19/30; C09K 19/12; G02F 1/133

[52] U.S. Cl. ................................. 252/299.63; 252/299.66

[58] Field of Search ...................... 252/299.63, 299.66; 349/182

[56] References Cited

U.S. PATENT DOCUMENTS

| | | | |
|---|---|---|---|
| 5,286,411 | 2/1994 | Rieger et al. | 252/299.63 |
| 5,292,454 | 3/1994 | Kurmeier et al. | 252/299.66 |
| 5,308,543 | 5/1994 | Sasaki et al. | 252/299.63 |
| 5,358,662 | 10/1994 | Hirose et al. | 252/299.63 |
| 5,368,772 | 11/1994 | Rieger et al. | 252/299.63 |
| 5,374,374 | 12/1994 | Weber et al. | 252/299.63 |
| 5,409,637 | 4/1995 | Rieger et al. | 252/299.63 |
| 5,480,581 | 1/1996 | Plaqch et al. | 252/299.63 |
| 5,487,845 | 1/1996 | Reiffenrath et al. | 252/299.63 |
| 5,498,365 | 3/1996 | Nolan et al. | 252/299.01 |
| 5,520,846 | 5/1996 | Plach et al. | 252/299.63 |
| 5,534,189 | 7/1996 | Nakagawa et al. | 252/299.63 |

*Primary Examiner*—C. H. Kelly
*Attorney, Agent, or Firm*—Wenderoth, Lind & Ponack L.L.P.

[57] ABSTRACT

Liquid crystal compositions which have excellent miscibility at low temperatures, a properly large optical anisotropy, and a small threshold voltage while satisfying various characteristics required of liquid crystal compositions for active matrix mode liquid crystal display devices. The compositions contain, as a first component, at least one compound expressed by any one of formulas

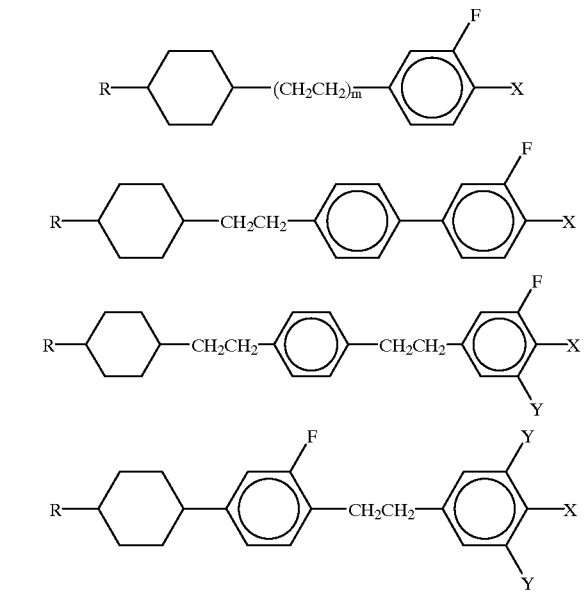

and as a second component, at least one compound expressed by any one of formulas

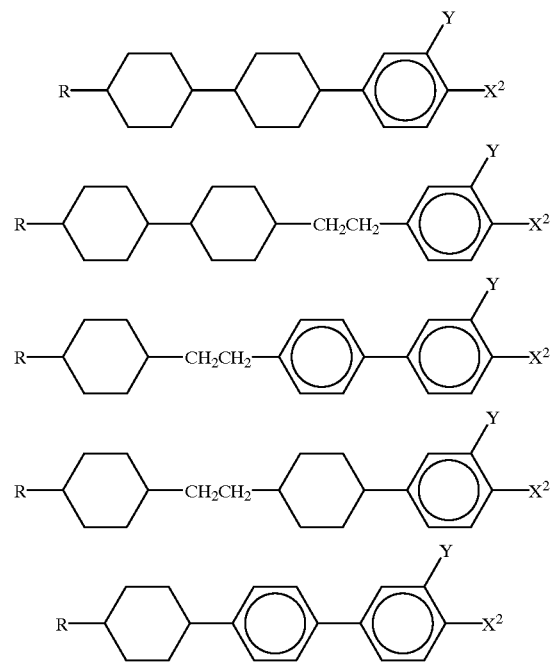

wherein R represents a straight chain alkyl group having 1 to 10 carbon atoms, X represents $CF_3$ or $OCF_3$, $X^2$ represents fluorine or $OCF_3$, each Y represents, independently of each other, a hydrogen or fluorine atom, and m is 1 or 2.

10 Claims, No Drawings

LIQUID CRYSTAL COMPOSITION AND LIQUID CRYSTAL DISPLAY DEVICE

TECHNICAL FIELD

The present invention relates to a nematic liquid crystal composition. More specifically, the present invention relates to a liquid crystal composition for an active matrix mode liquid crystal display device and a liquid crystal display device comprising the liquid crystal composition.

BACKGROUND ART

Liquid crystal display devices (LCD) have been produced by filling a liquid crystal composition in a sealed cell formed between two substrates provided with transparent electrodes. LCD have been practically used in various modes such as twist nematic (TN) mode, super twist nematic (STN) mode, and thin-film transistor (TFT) mode since their electric power consumption is small compared with CRT (cathode ray tube display) and since downsizing and weight-lightening are possible. Among the modes, active matrix LCD (AM-LCD) such as TFT have been watched as a prospective winner of flat display accompanied with the progress in actualization of colored display and fine picture image.

Following characteristics are required of the liquid crystal compositions for AM-LCD:

1) Proper optical anisotropy (Δn) can be produced depending on cell thickness.
2) Voltage holding ratio (VHR) is high to maintain a high contrast of LCD.
3) Electrooptical response speed is high to cope with dynamic image.
4) Range of nematic liquid crystal phase is wide depending on application environment (wide range).
5) Proper threshold voltage ($V_{th}$) can be obtained depending on driving circuit.

AM-LCD have been adopted for driving a TN display mode in which the molecular orientation of a liquid crystal composition filled between an upper and a lower substrate is twisted by 90°. In this TN display mode, coloring of liquid crystal cells due to interference caused when voltage is not applied is a problem. In order to avoid the coloring and to obtain an optimum contrast, the product (Δn·d) of Δn and cell thickness d ($\mu$m) must be established to a certain value, for example, to 0.5 $\mu$m. Since such restriction exists, a main current of Δn of liquid crystal compositions for TFT currently used in practice is generally about 0.07 to about 0.11 and particularly 0.08 to 0.10 for 1st. Min. system.

In recent years, demand for developing high response speed LCD is strong for the purpose of coping with dynamic image. Since response speed (τ) is proportional to the viscosity (η) of liquid crystal material, it is necessary to explore liquid crystal compositions of a low viscosity to achieve the high response speed.

With the development of portable LCD as a momentum, exploration for LCD intended for outdoor use has come to be investigated. In order to withstand outdoor use, liquid crystal compositions are considered to be necessary to exhibit a nematic phase over a range beyond the temperature range of application environment.

With respect to portable LCD, downsizing is desired to lessen their weight, whereas there are many restrictions in the aspect of driving electric power.

In order to cope with such situation, liquid crystal materials of small electric power consumption and low $V_{th}$ are desired. From such viewpoint, liquid crystal compositions having a nematic-isotropic phase transition temperature (clearing point $T_{NI}$) of 60° C. or higher and smectic-nematic phase transition temperature ($T_{SN}$) of lower than −20° C. have become a main stream of liquid crystal compositions for TFT currently used in practice.

In order to respond to such demand, various types of liquid crystalline compounds and liquid crystal compositions containing the compounds have been developed. For instance, Laid-open Japanese Patent Publication No. Hei 2-233626 has disclosed in its Application Example 2 a composition comprising 15% by weight of a trifluoro compound having a comparatively large dielectric anisotropy (Δε) and 85% by weight of a difluoro compound. However, this composition has defects that $V_{th}$ is high, the miscibility of the components in the composition is deteriorated particularly at low temperatures, and nematic phase range is narrow.

WO 94/03558 has disclosed compositions comprising a trifluoro compound and a difluoro compound. However, the compositions disclosed in its Examples 1 and 2 have such a low clearing point as lower than 50° C. and have a Δn of lower than 0.06, and thus are short of practical utility. Compositions disclosed in its Example 4 and after have a defect of having a high $V_{th}$.

Liquid crystal compositions are diligently being studied depending on various purposes as discussed above, they are still not sufficient, and it is a present situation that new improvements are all the time demanded.

DISCLOSURE OF THE INVENTION

An object of the present invention is to overcome the problems in the prior art mentioned above and to provide a liquid crystal composition which is excellent in miscibility at low temperatures, has a properly large Δn and has a low $V_{th}$ while satisfying various characteristics required of liquid crystal compositions for AM-LCD.

As a result of the investigation by the present inventors to achieve the objects mentioned above, the present invention has been accomplished.

BEST MODE FOR CARRYING OUT THE INVENTION

The liquid crystal composition of the present invention is characterized by containing, as a first component, at least one compound selected from the group consisting of the compounds expressed by any one of formulas (I-a) to (I-d)

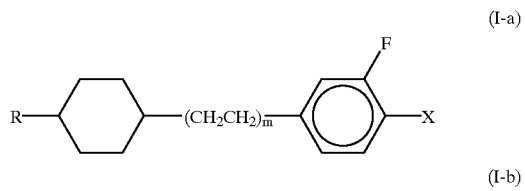

(I-a)

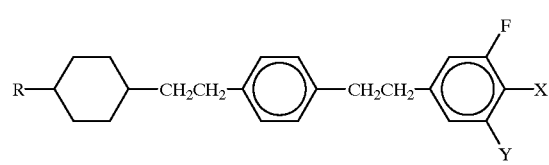

(I-b)

-continued (I-c)
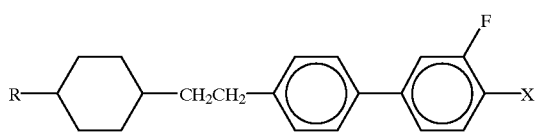

(I-d)
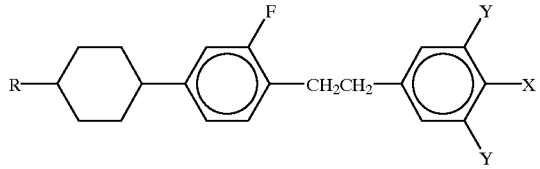

and containing, as a second component, at least one compound selected from the group consisting of the compounds expressed by any one of formulas (II-a) to (II-e)

(II-a)
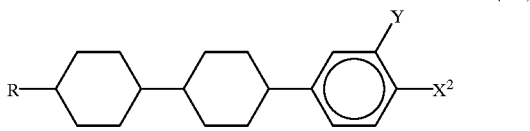

(II-b)
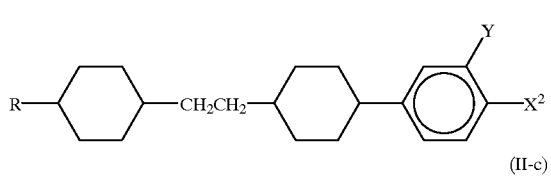

(II-c)
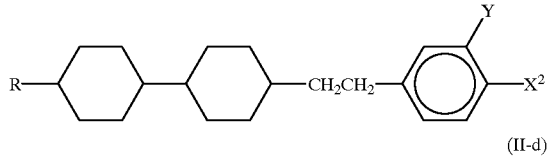

(II-d)
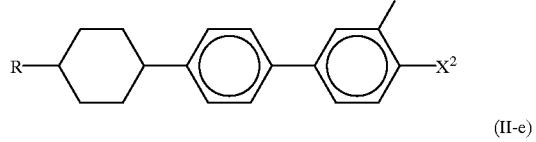

(II-e)
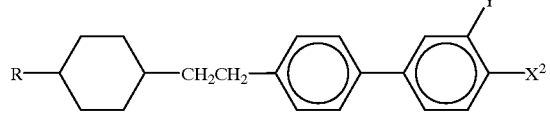

in each of the formulas mentioned above, R represents a straight chain alkyl group having 1 to 10 carbon atoms, X represents $CF_3$ or $OCF_3$, $X^2$ represents fluorine atom or $OCF_3$, Y represents or Ys independently with each other represent hydrogen atom or fluorine atom, and m is 1 or 2.

In the liquid crystal compositions of the present invention, the ratio of the amount of the first component to the amount of the second component in the total amount of the first component and the second component is preferably 3 to 40% by weight (first component) to 60 to 97% by weight (second component). Total amount of the first component and the second component is preferably 60 to 97% by weight based on the total amount of liquid crystal composition.

Liquid crystal composition of the present invention may further contain a compound of a first group expressed by the following formula (III), a compound of a second group expressed by formula (IV-a) or (IV-b), a compound of a third group expressed by formula (V-a) or (V-b), or a compound of fourth group expressed by any one of formulas (VI-a) to (VI-c).

Compound of the first group:

(III)
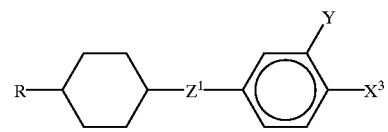

wherein R represents a straight chain alkyl group having 1 to 10 carbon atoms, $Z^1$ represents single bond or $—C_2H_4—$, $X^3$ represents fluorine atom or $OCF_3$, and Y represents hydrogen atom or fluorine atom.

Compound of the second group:

(IV-a)
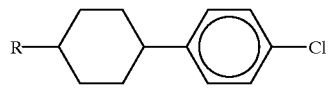

(IV-b)

in both of the formulas mentioned above, R represents a straight chain alkyl group having 1 to 10 carbon atoms.

Compound of the third group:

(V-a)
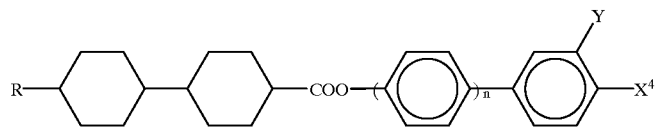

-continued

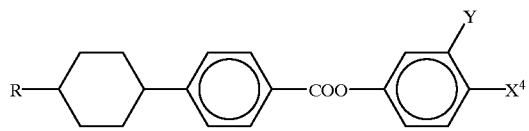
(V-b)

in both of the formula mentioned above, R represents a straight chain alkyl group having 1 to 10 carbon atoms, $X^4$ represents fluorine atom or $OCF_3$, Y represents hydrogen atom or fluorine atom, and n is 0 or 1.

Compound of the fourth group:

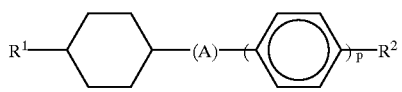
(VI-a)

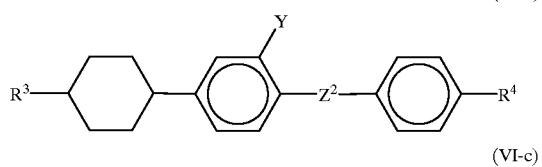
(VI-b)

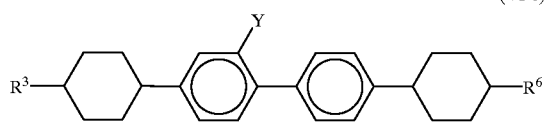
(VI-c)

in each of the formulas mentioned above, $R^1$, $R^3$, and $R^5$ represent an alkyl group or alkenyl group having 1 to 10 carbon atoms, any one or not adjacent two methylene groups (—$CH_2$—) in either of the alkyl group and alkenyl group may be replaced by oxygen atom (—O—), $R^2$, $R^4$, and $R^6$ represent an alkyl group or alkoxy group having 1 to 10 carbon atoms, A represents 1,4-cyclohexylene or 1,4-phenylene, $Z^2$ represents —CH=CH— or —C≡C—, Y represents hydrogen atom or fluorine atom, and p is 0 or 1.

By using these liquid crystal compositions of the present invention, liquid crystal display devices which satisfy the objects of the present invention can be obtained.

As preferable examples of the first component used in the liquid crystal compositions of the present invention, there can be mentioned compounds expressed by any one of formulas (I-a-1) to (I-a-4) with the compounds of formula (I-a); compounds expressed by any one of formulas (I-b-1) to (I-b-4) with the compounds of formula (I-b); compounds of formula (I-c-1) or (I-c-2) with the compounds of formula (I-c); and compounds expressed by any one of formulas (I-d-1) to (I-d-6) with the compounds of formula (I-d).

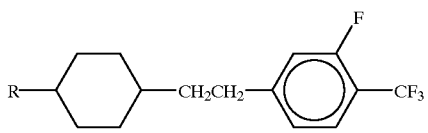
(I-a-1)

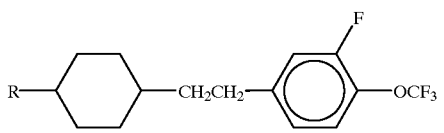
(I-a-2)

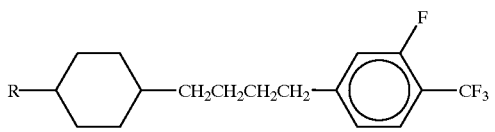
(I-a-3)

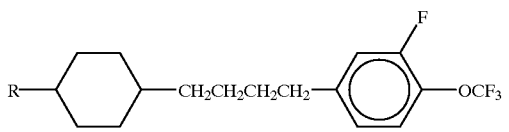
(I-a-4)

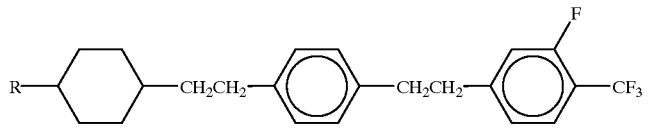
(I-b-1)
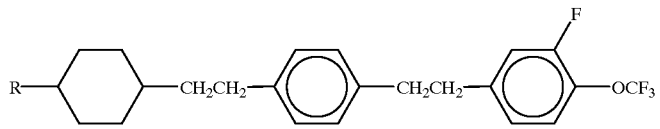
(I-b-2)
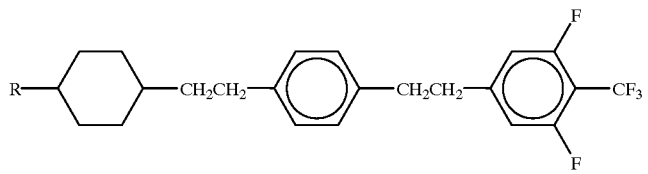
(I-b-3)
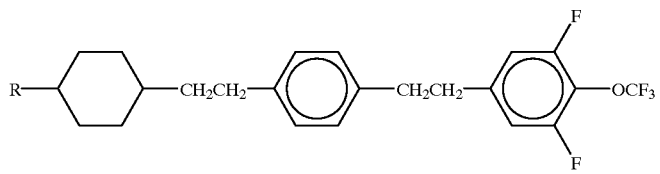
(I-b-4)
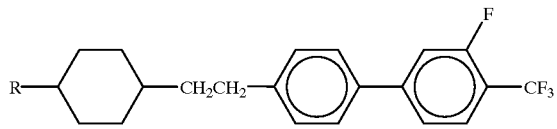
(I-c-1)
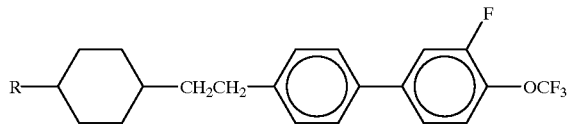
(I-c-2)
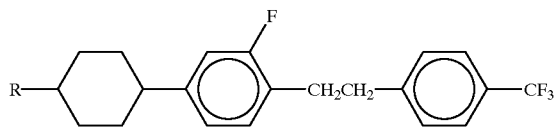
(I-d-1)
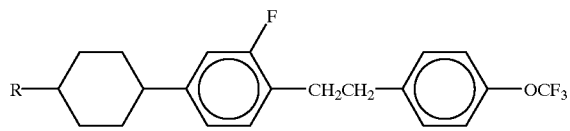
(I-d-2)
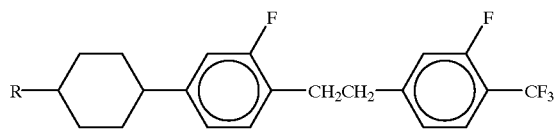
(I-d-3)
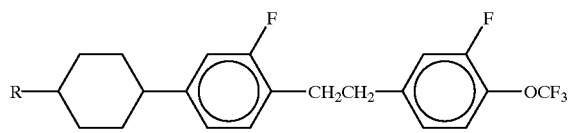
(I-d-4)

-continued

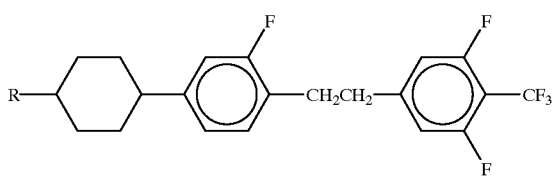
(I-d-5)

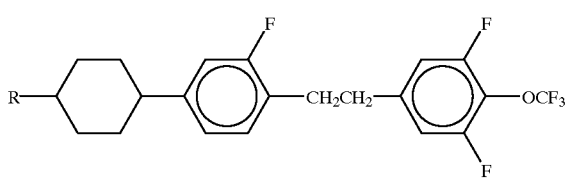
(I-d-6)

in each of the formulas shown above, R represents an alkyl group having 1 to 10 carbon atoms.

Among these compounds, particularly the ones expressed by any one of formulas (I-a-1), (I-a-3), (I-b-2), (I-b-3), (I-c-1), (I-c-2), and (I-d-4) are preferably used.

Whereas the compounds of the first group generally exhibit a large $\Delta\epsilon$ of 7 to 15, they have a low viscosity for their large $\Delta\epsilon$. Besides, since heat stability and chemical stability are excellent, the compounds of the first group particularly assume the role of reducing viscosity while maintaining $V_{th}$ of liquid crystal compositions for TFT.

Their content is generally 3 to 40% by weight and preferably 5 to 35% by weight based on the total amount of the first component and the second component. When the content is less than 3% by weight, effects such as an improvement in miscibility at low temperatures, a properly large $\Delta n$, and a low $V_{th}$ among the objects of the present invention come to be hardly achieved. Conversely, when the content exceeds 40% by weight, the viscosity of liquid crystal compositions becomes high and the miscibility at low temperatures is deteriorated both of which are unpreferable in the present invention.

As preferable examples of the second component used in the liquid crystal compositions of the present invention, there can be mentioned compounds expressed by any one of formulas (II-a-1) to (II-a-4) with the compounds of formula (II-a); compounds expressed by any one of formulas (II-b-1) to (II-b-4) with the compounds of formula (II-b); compounds expressed by any one of formulas (II-c-1) to (II-c-4) with the compounds of formula (II-c); compounds expressed by any one of formulas (II-d-1) to (II-d-4) with the compounds of formula (II-d); and compounds expressed by any one of formulas (II-e-1) to (II-e-4) with the compounds of formula (II-e).

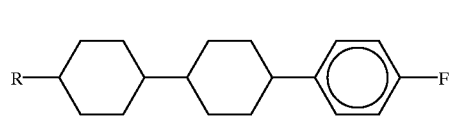
(II-a-1)

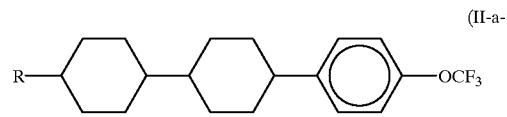
(II-a-2)

-continued

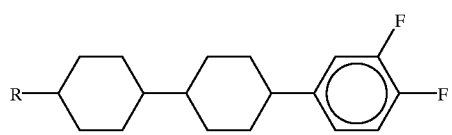
(II-a-3)

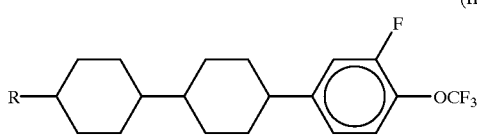
(II-a-4)

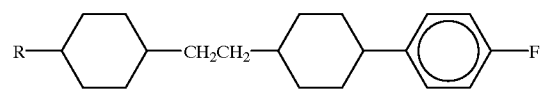
(II-b-1)

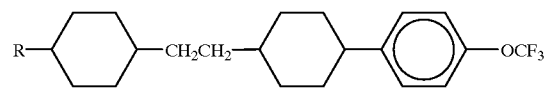
(II-b-2)

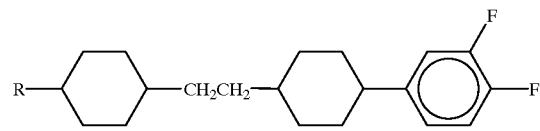
(II-b-3)

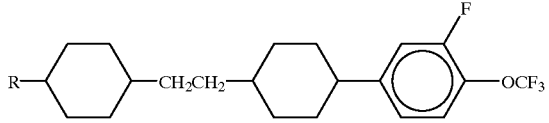
(II-b-4)

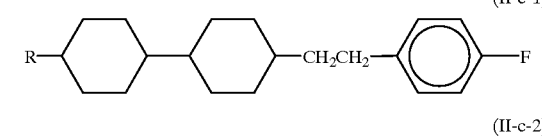
(II-c-1)

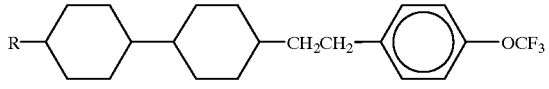
(II-c-2)

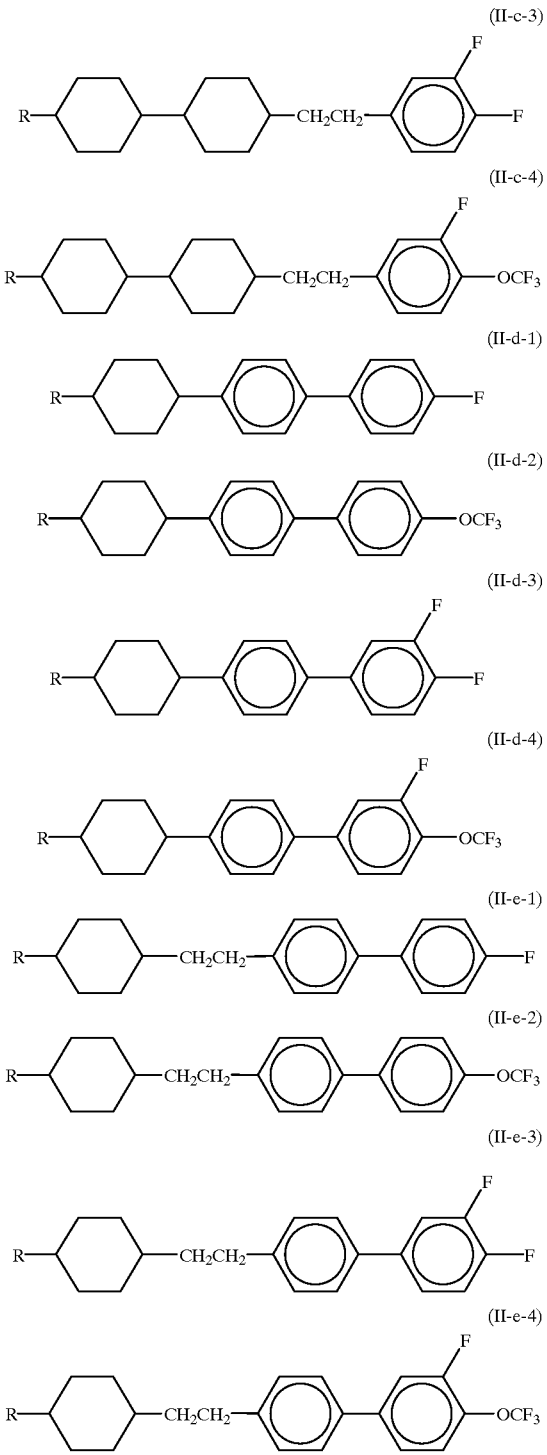

clearing point ($T_{NI}$) is in the range of about 90 to about 130° C., they are most suitable for the base compound of liquid crystal compositions for low voltage TFT.

Their content is generally 60 to 97% by weight and preferably 65 to 95% by weight based on the total amount of the first component and the second component. When the content is less than 60% by weight, the miscibility of liquid crystal compositions is sometimes deteriorated particularly at low temperatures. Conversely, when the content exceeds 97% by weight, the effect of viscosity reduction of liquid crystal compositions comes to be hardly achieved.

Among the compounds of the first to the fourth groups which can be further added to the liquid crystal compositions of the present invention, the compounds expressed by any one of the following formulas (III-1) to (III-8) can be mentioned as preferable examples of the compounds of the first group expressed by formula (III).

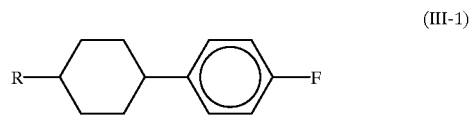

(III-1)

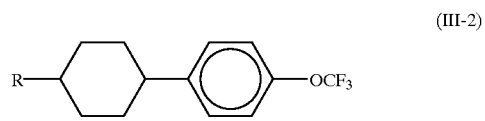

(III-2)

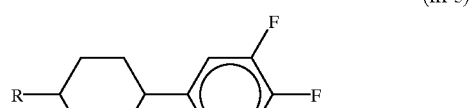

(III-3)

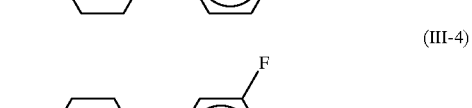

(III-4)

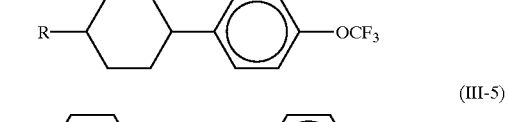

(III-5)

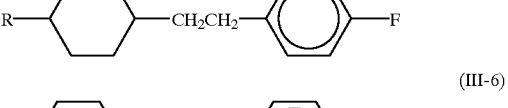

(III-6)

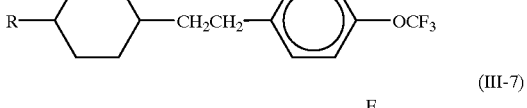

(III-7)

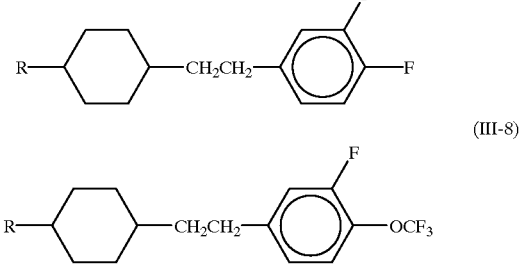

(III-8)

in each of the formulas shown above, R represents an alkyl group having 1 to 10 carbon atoms.

Among these compounds, particularly the ones expressed by any one of formulas (II-a-1), (II-a-2), (II-a-3), (II-b-2), (II-b-3), (II-c-2), (II-d-1), (II-d-3), and (II-e-3) are preferably used.

Since the compounds of the second group have a Δε value generally in the range 5 to 8, and excellent heat and chemical stability, they are well known as preferable compounds for the liquid crystal compositions for TFT. In addition, since wherein R represents an alkyl group having 1 to 10 carbon atoms.

Among these compounds, particularly the ones expressed by formula (III-1), (III-3), or (III-5) are preferably used.

Compounds of the first group are bicyclic ones and particularly assume the role of lowering the $V_{th}$ of liquid crystal compositions. In order to prevent the excessive lowering of the clearing point of liquid crystal compositions, their content is preferably adjusted to less than 15% by weight based on the total amount of liquid crystal composition.

Compounds expressed by formula (IV-a) or (IV-b) of the second group are bi- or tricyclic compounds containing chlorine (Cl) and mainly assume the role of reducing the viscosity of liquid crystal compositions. Since these compounds have a small $\Delta\epsilon$ of 4 to 5, $V_{th}$ of liquid crystal compositions is sometimes heightened when they are used in a large amount. Accordingly, the content is preferably less than 35% by weight based on the total amount of liquid crystal composition.

As preferable examples of the compounds of the third group, there can be mentioned the compounds expressed by any one of formulas (V-a-1) to (V-a-8) with the compounds of formula (V-a) and the compounds expressed by any one of formulas (V-b-1) to (V-b-4) with the compounds of formula (V-b).

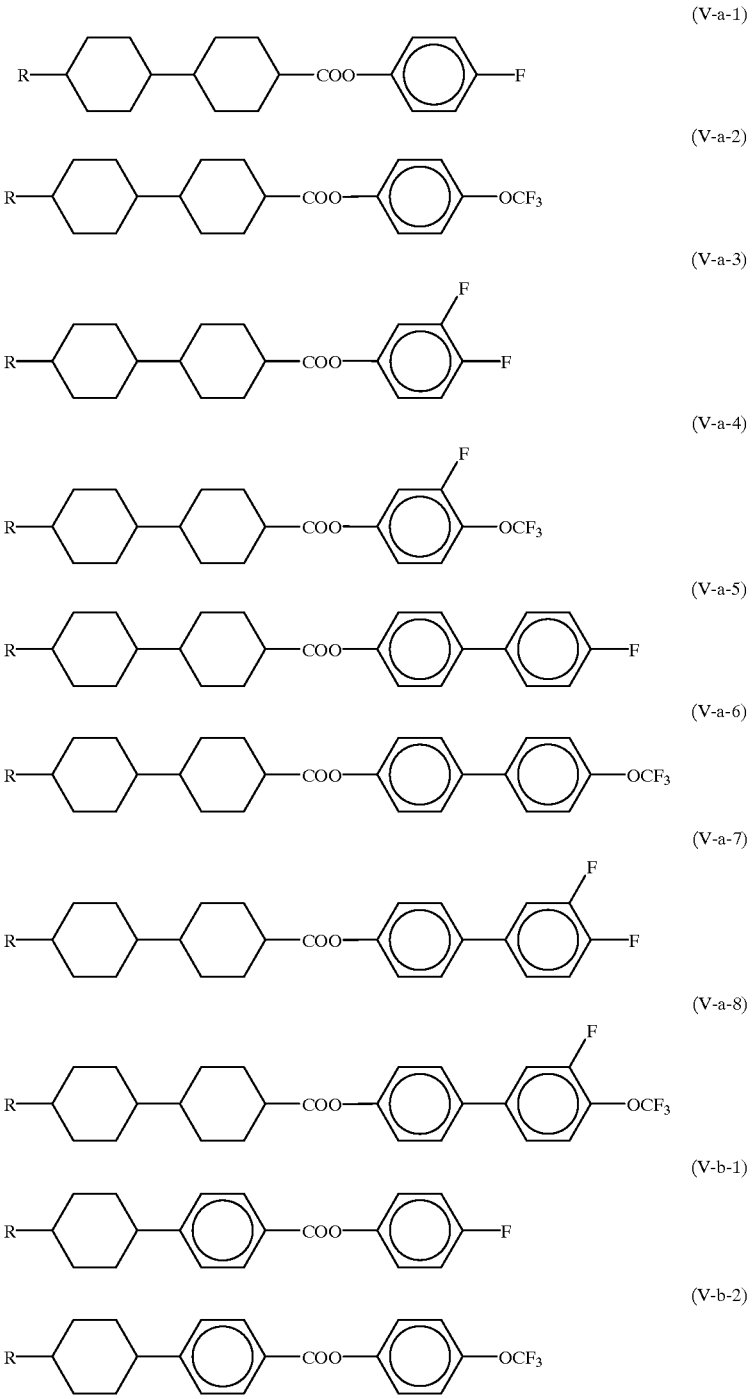

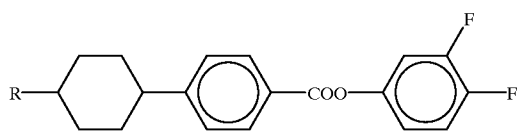

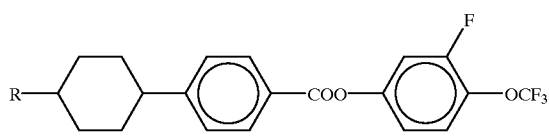

in each of the formulas shown above, R represents an alkyl group having 1 to 10 carbon atoms.

Among these compounds, particularly the compounds expressed by formula (V-a-1), (V-a-5), or (V-b-1) are preferably used.

Since these compounds of the third group have a Δε value in the range of about 5 to about 8, and excellent heat and chemical stability, they are well known as preferable compounds for the liquid crystal compositions for TFT. In addition, since clearing point ($T_{NI}$) is in the range of about 90 to about 130° C., they are most suitable for base compound of the liquid crystal compositions for low voltage TFT.

Their content is generally less than 40% by weight and preferably less than 30% by weight based on the total amount of liquid crystal composition. When the content exceeds 40% by weight, viscosity reduction effect which is an object of the present invention comes to be hardly achieved.

As preferable examples of the compounds of the fourth group, there can be mentioned the compounds expressed by any one of formulas (VI-a-1) to (VI-a-9) with the compounds of formula (VI-a); compounds expressed by any one of formulas (VI-b-1) to (VI-b-4) with the compounds of formula (VI-b); and compounds expressed by any one of formulas (VI-c-1) to (VI-c-3) with the compounds of formula (VI-c).

(VI-a-1)
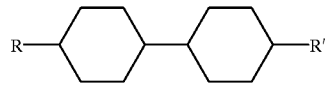

(VI-a-2)
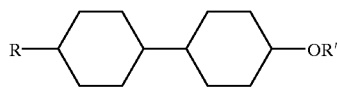

(VI-a-3)
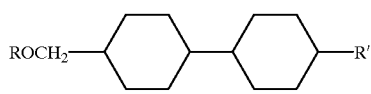

(VI-a-4)
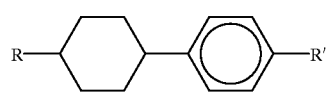

(V-b-3)

(V-b-4)

-continued (VI-a-5)
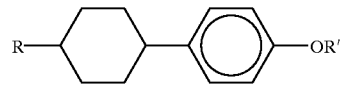

(VI-a-6)
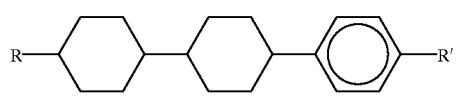

(VI-a-7)
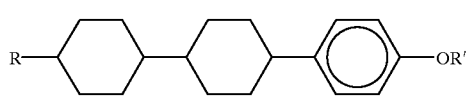

(VI-a-8)
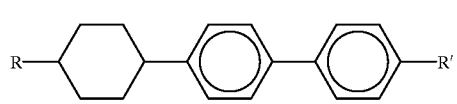

(VI-a-9)

(VI-b-1)
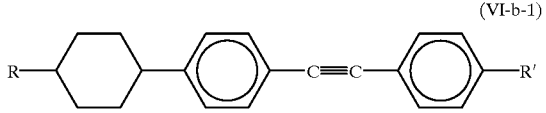

(VI-b-2)
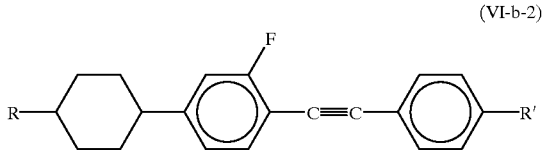

(VI-b-3)
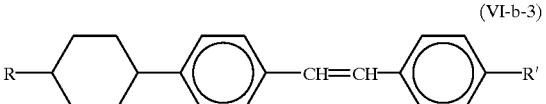

(VI-b-4)
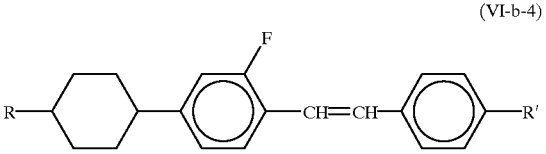

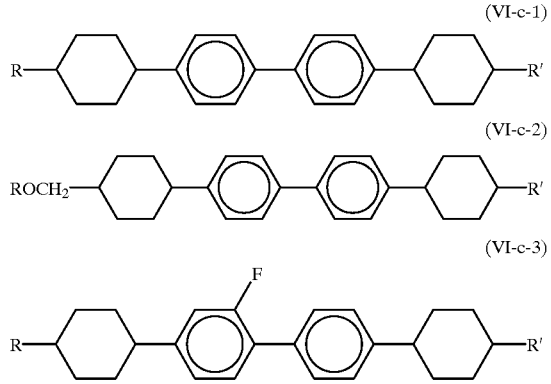

in each of the formulas shown above, R and R' independently of each other represent an alkyl group or alkenyl group.

Among these compounds, the compounds expressed particularly in any one of formulas (VI-a-1), (VI-a-3), (VI-a-5), (VI-a-6), (VI-a-7), (VI-b-2), (VI-b-4), and (VI-c-2) are preferably used.

These compounds of the fourth group have a bi-, tri-, or tetracyclic structure, and exhibit negative or small positive $\Delta\epsilon$.

Among these compounds, bi- or tricyclic compounds are used for the purpose mainly of reducing viscosity and/or adjusting $\Delta n$ of liquid crystal compositions. Tetracyclic compounds are used for the purpose of widening nematic range, for instance, by raising clearing point ($T_{NI}$) and/or the purpose of adjusting $\Delta n$ and viscosity.

Liquid crystal compositions of the present invention may contain an adequate amount of other compounds for improving the objects of the present invention, for example, to improve $V_{th}$, nematic range, $\Delta n$, $\Delta\epsilon$, and viscosity, in addition to the compounds of the first group to the fourth group mentioned above.

Liquid crystal compositions of the present invention are produced by methods conventional in the art, for instance, by a method in which various components are dissolved in each other at a high temperature, and a method in which various components are dissolved in an organic solvent to mix them and then the solvent is distilled off under a reduced pressure.

Also, when desired, the liquid crystal compositions of the present invention are improved to optimize their effect depending on the applications intended, by adding a suitable additive. Such additives are well known in the art and described in detail in literatures. Usually, a chiral dopant or the like is added to cause a helical structure of liquid crystal to adjust a required twisting angle and to avoid reverse-twist.

Further, the liquid crystal compositions of the present invention can be used for guest-host (GH) mode when a dichroic dye such as merocyanine type, styryl type, azo type, azomethine type, azoxy type, quinophthalone type, anthraquinone type, and tetrazine type is added.

Liquid crystal compositions of the present invention can be used even for polymer dispersion type liquid crystal display devices (PDLCD) typified by NCAP which is prepared by forming a nematic liquid crystal into a microcapsule or typified by a polymer network liquid crystal display device (PNLCD) which is prepared by forming a polymer of three-dimensional network structure in a liquid crystal; for electrically controlled birefringence (ECB) mode; and for dynamic scattering (DS) mode.

According to the present invention, liquid crystal compositions can be provided which are excellent particularly in miscibility at low temperatures, have a properly large $\Delta n$, and have a low $V_{th}$ while satisfying various characteristics required of the liquid crystal compositions for AM-LCD.

Now, the present invention will be described in more detail with reference to Examples. However, it should be understood that the present invention is by no means restricted by such specific Examples.

In the following Examples, compounds are designated according to the understanding shown in Table 1 below. That is, left side terminal group is expressed by n-, nO-, nOm-, Vn-, nVm-, or nVmVk- (n, m, and k are an integer of 1 or more); bonding group is expressed by 2, E, T, V, or CF2O; ring structure is expressed by B, B(F), B(F,F), H, Py, D, or Ch; and right side terminal group is expressed by —F, -CL, —C, —CF3, —OCF3, —OCF2H, -n, -On, or -EMe (in which n and m are an integer of 1 or more). The % showing the content of each compound means % by weight unless otherwise specified.

Characteristics data of liquid crystal compositions were shown by $T_{NI}$ (clearing point), $T_{SN}$ (smectic-nematic phase transition point), η20 (viscosity at 20° C.), $\Delta n$ (optical anisotropy at 25° C.), $\Delta\epsilon$ (dielectric anisotropy at 25° C.), $V_{th}$ (threshold voltage at 20° C.), and VHR at 25° C. (voltage holding ratio determined by "Area Method"). $T_{SN}$ mentioned above was judged by liquid crystal phase after a liquid crystal composition was left in each of freezers kept at 0° C., –10° C., –20° C., or –30° C. for 30 days.

TABLE 1

| Left side terminal group | Symbol | Bonding group | Symbol |
|---|---|---|---|
| $C_nH_{2n+1}$— | n- | —$CH_2CH_2$— | 2 |
| $C_nH_{2n+1}O$— | nO- | —COO— | E |
| $C_nH_{2n+1}OC_mH_{2m}$— | nOm- | —C≡C— | T |
| $CH_2$=$CHC_nH_{2n}$— | Vn- | —CH=CH— | V |
| $C_nH_{2n+1}CH$=$CHC_mH_{2m}$— | nVm- | —$CF_2O$— | CF2O |
| $C_nH_{2n+1}CH$=$CHC_mH_{2m}CH$=$CHC_kH_{2k}$— | nVmVk- | | |

TABLE 1-continued

| Ring structure | Symbol | Right side terminal group | Symbol |
|---|---|---|---|
|  | B | —F | —F |
| 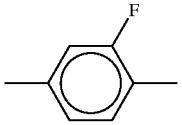 | B(F) | —Cl | —CL |
| 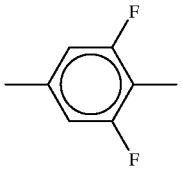 | B(F,F) | —CN<br>—CF$_3$ | —C<br>—CF3 |
|  | H | —OCF$_3$ | —OCF3 |
|  | Py | —OCF$_2$H | —OCF2H |
| 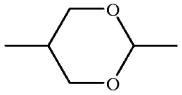 | D | —C$_n$H$_{2n+1}$ | -n |
| 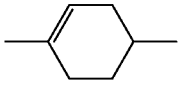 | Ch | —OC$_n$H$_{2n+1}$<br>—COOCH$_3$ | —On<br>—EMe |

COMPARATIVE EXAMPLE 1

Application Example 2 in the Laid-open Japanese Patent Publication No. Hei 2-233626 mentioned above has disclosed the liquid crystal composition comprising the following compounds:

3-HHB(F,F)-F 15.0%
2-HHB(F)-F 28.4%
3-HHB(F)-F 28.3%
5-HHB(F)-F 28.3%

Characteristics of the composition were determined and the results were as follows:

$T_{NI}$=110.7° C.
$T_{SN}$<0° C.
η20=25.0 mPa·s
Δn=0.077
$V_{th}$=2.32 V
VHR=98.8%

As will be clear from the results mentioned above, the liquid crystal composition of Comparative Example 1 has a high $V_{th}$, is not good in miscibility at low temperatures ($T_{SN}$ is high), and besides, exhibits a slightly small Δn, and thus this composition is considered to be insufficient in practical utility.

COMPARATIVE EXAMPLE 2

Example 1 in the WO 94/03558 mentioned above has disclosed the liquid crystal composition comprising the following compounds:

7-HB(F,F)-F 10.0%
2-HHB(F,F)-F 25.0%
3-HHB (F,F)-F 35.0%
5-HHB(F,F)-F 18.0%
7-HB (F)-F 12.0%

Characteristics of the composition were determined and the results were as follows:

$T_{NI}$=42.9° C.
$T_{SN}$<0° C.
η20=22.2 mPa·s
Δn=0.059
$V_{th}$=1.07 V
VHR=98.7%

As will be clear from the results mentioned above, whereas the liquid crystal composition of Comparative Example 2 has a low $V_{th}$, it has a low $T_{NI}$ (clearing point), is not good in miscibility at low temperatures ($T_{SN}$ is high), and besides, exhibits a small Δn, and thus this composition is considered to be insufficient in practical utility.

COMPARATIVE EXAMPLE 3

Example 2 in the WO 94/03558 mentioned in Comparative Example 2 has disclosed the liquid crystal composition comprising the following compounds:

2-HHB(F,F)-F 26.0%
3-HHB(F,F)-F 26.0%
5-HHB(F,F)-F 26.0%
7-HB(F)-F 12.0%
5-H2B(F)-F 10.0%

Characteristics of the composition were determined and the results were as follows:

$T_{NI}$=46.0° C.
$T_{SN}$<0° C.
$\eta 20$=21.6 mPa·s
$\Delta n$=0.058
$V_{th}$=1.17 V
VHR=98.5%

As will be clear from the results mentioned above, whereas the liquid crystal composition of Comparative Example 3 has a low $V_{th}$, it has a low $T_{NI}$ (clearing point), is not good in miscibility at low temperatures ($T_{SN}$ is high), and besides, exhibits a small $\Delta n$, and thus this composition is considered to be insufficient in practical utility.

Example 1

Liquid crystal composition comprising the following compounds was prepared:

3-H2B(F)-CF3 5.0%
2-HHB(F)-F 10.0%
3-HHB(F)-F 10.0%
5-HHB(F)-F 10.0%
2-H2HB (F)-F 14.0%
3-H2HB(F)-F 7.0%
5-H2HB(F)-F 14.0%
2-HBB(F)-F 7.5%
3-HBB(F)-F 7.5%
5-HBB(F)-F 15.0%

Characteristics of the composition were determined and the results were as follows:

$T_{NI}$=86.6° C.
$T_{SN}$<-30° C.
$\eta 20$=25.4 mPa·s
$\Delta n$=0.092
$\Delta \epsilon$=5.3
$V_{th}$=2.10 V
VHR=98.6%

As will be seen from the results mentioned above, the liquid crystal composition of this Example is remarkably excellent in miscibility at low temperatures compared with that in Comparative Examples 1 to 3 ($T_{SN}$ is low) and besides it has a large $\Delta n$. While $T_{NI}$ (clearing point) is high such an extent that causes practically no problem, $V_{th}$ of the composition can be found to be small compared with that in Comparative Example 1.

Example 2

Liquid crystal composition comprising the following compounds was prepared:

3-H2BB(F)-CF3 15.0%
3-H2H2B(F)-OCF3 10.0%
3-H2H2B(F,F)-CF3 10.0%
2-HHB(F)-F 10.0%
3-HHB(F)-F 10.0%
5-HHB(F)-F 10.0%
2-H2HB(F)-F 6.0%
3-H2HB(F)-F 3.0%
5-H2HB(F)-F 6.0%
2-HBB(F)-F 4.0%
3-HBB(F)-F 4.0%
5-HBB(F)-F 8.0%
7-HB(F)-F 4.0%

Characteristics of the composition were determined and the results were as follows:

$T_{NI}$=86.3° C.
$T_{SN}$<-30° C.
$\eta 20$=25.3 mPa·s
$\Delta n$=0.091
$\Delta \epsilon$=5.4
$V_{th}$=2.13 V
VHR=98.5%

As will be seen from the results mentioned above, the liquid crystal composition of this Example is remarkably excellent in miscibility at low temperatures compared with that in Comparative Examples 1 to 3 ($T_{SN}$ is low) and besides it has a large $\Delta n$. While $T_{NI}$ (clearing point) is high such an extent that causes practically no problem, $V_{th}$ of the composition can be found to be small compared with that in Comparative Example 1.

Example 3

Liquid crystal composition comprising the following compounds was prepared:

3-H2B(F)-CF3 5.0%
3-HB(F)2B(F)-OCF3 10.0%
2-HHB(F)-F 13.4%
3-HHB(F)-F 13.3%
5-HHB(F)-F 13.3%
3-HHB-OCF3 8.0%
2-H2HB(F)-F 4.0%
3-H2HB(F)-F 2.0%
5-H2HB(F)-F 4.0%
3-H2HB-OCF3 3.0%
5-HH2B-OCF3 5.0%
7-HB-F 4.0%
7-HB(F)-F 7.0%
5-H2HB(F,F)-F 3.0%
3-HH2B(F,F)-F 5.0%

Characteristics of the composition were determined and the results were as follows:

$T_{NI}$=66.0° C.
$T_{SN}$<-30° C.
$\eta 20$=18.9 mPa·s
$\Delta n$=0.080
$\Delta \epsilon$=5.2
$V_{th}$=1.92 V
VHR=98.7%

As will be seen from the results mentioned above, the liquid crystal composition of this Example is remarkably excellent in miscibility at low temperatures compared with that in Comparative Examples 1 to 3 ($T_{SN}$ is low) and besides it has a large Δn. While $T_{NI}$ (clearing point) is high such an extent that causes practically no problem, $V_{th}$ of the composition can be found to be small compared with that in Comparative Example 1.

Example 4

Liquid crystal composition comprising the following compounds was prepared:

5-H2B(F)-CF3 10.0%
3-H2BB(F)-CF3 5.0%
3-H2H2B(F)-OCF3 3.0%
3-HHB-F 4.0%
2-HHB(F)-F 6.0%
3-HHB(F)-F 6.0%
5-HHB(F)-F 6.0%
3-H2HB-OCF3 4.0%
5-H2HB-OCF3 4.0%
2-HBB-F 4.0%
3-HBB-F 4.0%
2-HBB(F)-F 6.0%
3-HBB(F)-F 6.0%
5-HBB(F)-F 12.0%
7-HB(F)-F 4.0%
5-H2B(F)-F 2.0%
3-HB(F)VB-2 4.0%
3-HB(F)T-3 4.0%
3-HB(F)T-4 3.0%
7-HB(F,F)-F 3.0%

Characteristics of the composition were determined and the results were as follows:

$T_{NI}$=81.5° C.
$T_{SN}$<-30° C.
η20=22.4 mPa·s
Δn=0.103
Δε=5.1
$V_{th}$=2.10 V
VHR=98.5%

Example 5

Liquid crystal composition comprising the following compounds was prepared:

3-H2B (F)-CF3 5.0%
3-H2H2B(F,F)-CF3 4.0%
2-HHB(F)-F 8.0%
3-HHB(F)-F 8.0%
5-HHB(F)-F 8.0%
3-H2HB(F)-F 6.0%
5-H2HB(F)-F 6.0%
2-H2HB-OCF3 5.0%
3-H2HB-OCF3 5.0%
5-HH2B-OCF3 4.0%
2-HBB(F)-F 2.5%
3-HBB(F)-F 2.5%
5-HBB(F)-F 5.0%
5-HHEBB-F 2.0%
3-HBEB-F 3.0%
5-HEB-F 2.5%
7-HEB-F 2.5%
3-HHB (F,F)-F 8.0%
3-H2HB(F,F)-F 4.0 $
3-HH2B(F,F)-F 5.0%
5-HH2B(F,F)-F 4.0%

Characteristics of the composition were determined and the results were as follows:

$T_{NI}$=91.6° C.
$T_{SN}$<-30° C.
η20=23.8 mPa·s
Δn=0.084
Δε=6.1
$V_{th}$=2.08 V
VHR=98.8%

Example 6

Liquid crystal composition comprising the following compounds was prepared:

3-HB(F)2B(F)-OCF3 5.0%
3-HHB-F 6.0%
2-HHB(F)-F 7.0%
3-HHB(F)-F 7.0%
5-HHB(F)-F 7.0%
3-HH2B-OCF3 4.0%
5-HH2B-OCF3 6.0%
2-HBB(F)-F 6.0%
3-HBB(F)-F 6.0%
5-HBB(F)-F 12.0%
7-HB(F)-F 6.0%
3-HHEBB-F 3.0%
5-HHEBB-F 3.0%
3-HB-O2 8.0%
3-HHB-1 4.0%
3-HHB-O1 2.0%
V-HHB-1 2.0%
3-HH-4 4.0%
101-HH5 2.0%

Characteristics of the composition were determined and the results were as follows:

$T_{NI}$=104.8° C.
$T_{SN}$<-30° C.
η20=20.0 mPa·s
Δn=0.097
Δε=3.9
$V_{th}$=2.30 V
VHR=98.6%

Example 7

Liquid crystal composition comprising the following compounds was prepared:

3-H2H2B(F)-OCF3 5.0%
2-HHB(F)-F 9.0%
3-HHB(F)-F 9.0%
5-HHB(F)-F 9.0%
2-H2HB(F)-F 4.0%
3-H2HB(F)-F 2.0%
5-H2HB(F)-F 4.0%
3-HBB-F 2.0%

2-HBB(F)-F 4.0%
3-HBB(F)-F 4.0%
5-HBB(F)-F 8.0%
3-H2BB(F)-F 8.0%
3-HB-CL 6.0%
5-HB-CL 6.0%
7-HB-CL 6.0%
2-HHB-CL 6.0%
3-HHB-CL 4.0%
5-HHB-CL 4.0%

Characteristics of the composition were determined and the results were as follows:

$T_{NI}$=89.0° C.
$T_{SN}$<-20° C.
η20=20.2 mPa·s
Δn=0.101
Δε=4.7
$V_{th}$=2.31 V
VHR=98.7%

Example 8

Liquid crystal composition comprising the following compounds was prepared:

5-H2B(F)-CF3 10.0%
3-H2BB(F)-OCF3 10.0%
3-HHB-F 5.0%
2-HHB(F)-F 12.0%
3-HHB(F)-F 12.0%
5-HHB(F)-F 12.0%
3-HH2B-OCF3 3.0%
2-HB B(F)-F 4.0%
3-HBB(F)-F 4.0%
5-HBB(F)-F 8.0%
3-HB-O2 10.0%
3-HHB-1 4.0%
3-HHB-O1 3.0%
101-HBBH-3 3.0%

Characteristics of the composition were determined and the results were as follows:

$T_{NI}$=90.6° C.
$T_{SN}$<-30° C.
η20=21.8 mPa·s
Δn=0.099
Δε=4.9
$V_{th}$=2.29 V
VHR=98.9%

Example 9

Liquid crystal composition comprising the following compounds was prepared:

3-H2B(F)-CF3 3.0%
5-H2B(F)-CF3 3.0%
3-H2BB (F)-CF3 3.0%
2-HHB(F)-F 12.0%
3-HHB(F)-F 12.0%
5-HHB(F)-F 12.0%
2-H2HB(F)-F 8.0%
3-H2HB(F)-F 4.0%
5-H2HB(F)-F 8.0%
2-HBB(F)-F 5.0%
3-HBB(F)-F 5.0%
5-HBB(F)-F 10.0%
3-HBEB-F 5.0%
3-HHEB-F 5.0%
5-HHEB-F 5.0%

Characteristics of the composition were determined and the results were as follows:

$T_{NI}$=98.1° C.
$T_{SN}$<-30° C.
η20=26.6 mPa·s
Δn=0.094
Δε=5.6
$V_{th}$=2.12 V
VHR=98.3%

Example 10

Liquid crystal composition comprising the following compounds was prepared:

5-H2B(F)-CF3 6.0%
2-HHB(F)-F 10.0%
3-HHB(F)-F 10.0%
5-HHB(F)-F 10.0%
2-H2HB(F)-F 6.0%
3-H2HB(F)-F 3.0%
5-H2HB(F)-F 6.0%
3-HH2B-OCF3 5.0%
2-HBB(F)-F 2.5%
3-HBB(F)-F 2.5%
5-HBB(F)-F 5.0%
5-HB-F 6.0%
7-HB(F)-F 6.0%
3-HB-CL 4.0%
3-HHEB-F 2.0%
3-HBEB-F 2.0%
3-HH-5 3.0%
101-HH-5 3.0%
3-HB-O4 4.0%
3-H2BB (F,F)-F 4.0%

Characteristics of the composition were determined and the results were as follows:

$T_{NI}$=98.2° C.
$T_{SN}$<-30° C.
η20=17.3 mPa·s
Δn=0.083
Δε=5.5
$V_{th}$=2.10 V
VHR=98.8%

Example 11

Liquid crystal composition comprising the following compounds was prepared:

5-H2B(F)-CF3 3.0%
3-H4B(F)-CF3 3.0%
2-HHB(F)-F 10.0%
3-HHB(F)-F 10.0%
5-HHB(F)-F 10.0%

2-H2HB(F)-F 6.0%
3-H2HB(F)-F 3.0%
5-H2HB(F)-F 6.0%
3-HH2B-OCF3 5.0%
2-HBB(F)-F 2.5%
3-HBB(F)-F 2.5%
5-HBB(F)-F 5.0%
5-HB-F 6.0%
7-HB(F)-F 6.0%
3-HB-CL 4.0%
3-HHEB-F 2.0%
3-HBEB-F 2.0%
3-HH-5 3.0%
101-HH-5 3.0%
3-HB-O4 4.0%
3-H2BB(F,F)-F 4.0%

What is claimed is:

1. A liquid crystal composition containing, as a first component, 3 to 40% by weight of at least one compound selected from the group consisting of the compounds expressed by any one of formulas (I-a) to (I-d)

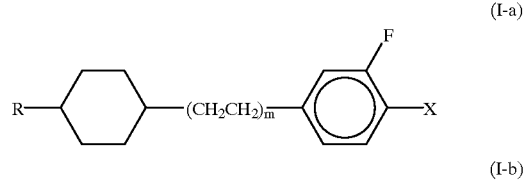
(I-a)

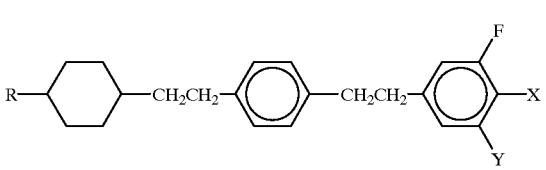
(I-b)

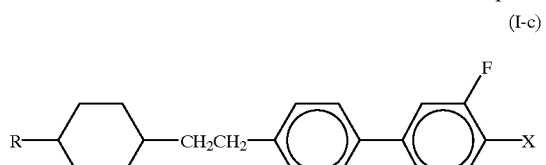
(I-c)

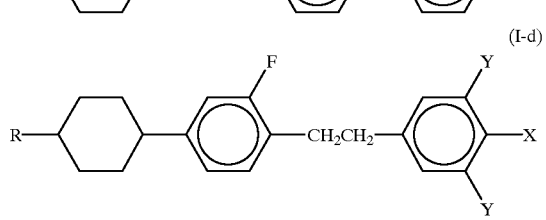
(I-d)

and containing, as a second component, 60 to 97% by weight of at least one compound selected from the group consisting of the compounds expressed by any one of formulas (II-a) to (II-e)

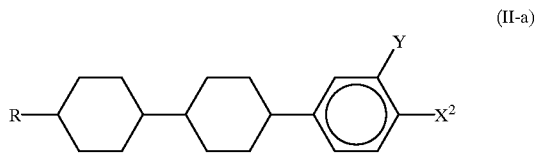
(II-a)

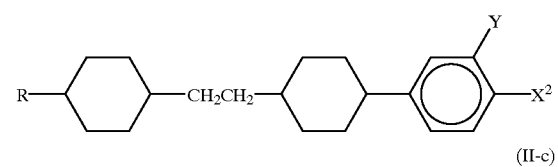
(II-b)

(II-c)

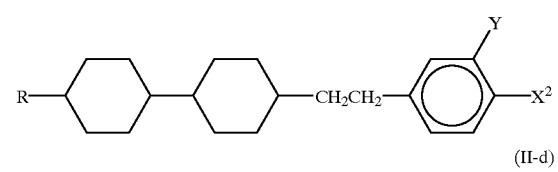

(II-d)

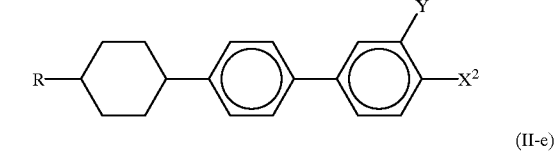

(II-e)

where in each of the formulas above, R represents a straight chain alkyl group having 1 to 10 carbon atoms, X represents $CF_3$ or $OCF_3$, $X^2$ represents fluorine atom or $OCF_3$, each Y independently represents hydrogen atom or fluorine atom, and m is 1 or 2.

2. The liquid crystalline composition according to claim 1 wherein the total amount of the first component and the second component is 60 to 97% by weight based on the total amount of the liquid crystal composition.

3. The liquid crystal composition according to claim 1 wherein the liquid crystal composition further contains at least one compound expressed by formula (IV-a) or (IV-b)

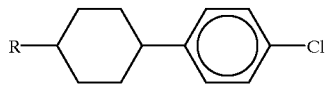
(IV-a)

(IV-b)

where in each of the formulas above, R represents a straight chain alkyl group having 1 to 10 carbon atoms.

4. The liquid crystal composition according to claim 1 wherein the liquid crystal composition further contains at least one compound expressed by formula (V-a) or (V-b)

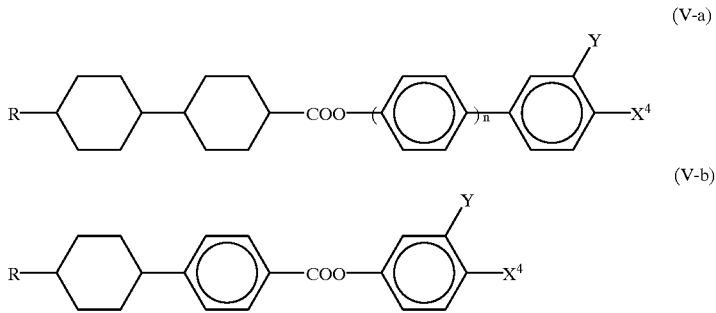

where in each of the formulas above, R represents a straight chain alkyl group having 1 to 10 carbon atoms, $X^4$ represents fluorine atom or $OCF_3$, Y represents hydrogen atom or fluorine atom, and n is 0 or 1.

5. The liquid crystal composition according to claim 1 wherein the liquid crystal composition further contains at least one compound selected from the group consisting of the compounds expressed by any one of formulas (VI-a) to (VI-c)

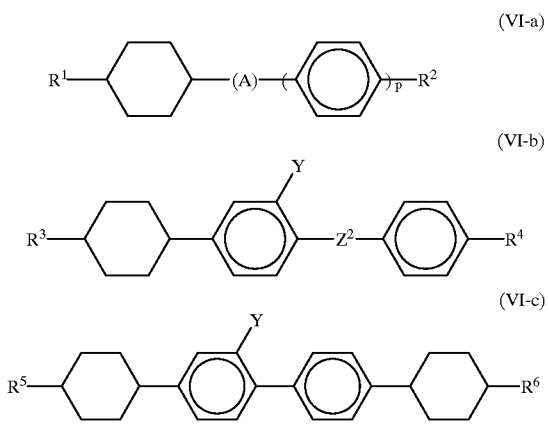

where in each of the formulas above, $R^1$, $R^3$, and $R^5$ represent an alkyl group or alkenyl group having 1 to 10 carbon atoms, any one or not adjacent two methylene groups ($-CH_2-$) in either of the alkyl group and alkenyl group may be replaced by oxygen atom ($-O-$), $R^2$, $R^4$, and $R^6$ represent an alkyl group or alkoxy group having 1 to 10 carbon atoms, A represents 1,4-cyclohexylene or 1,4-phenylene, $Z^2$ represents $-CH=CH-$ or $-C\equiv C-$, Y represents hydrogen atom or fluorine atom, and p is 0 or 1.

6. A liquid crystal display de ice comprising a liquid crystal composition defined in claim 1.

7. A liquid crystal display device comprising a liquid crystal composition defined in claim 2.

8. A liquid crystal display device comprising a liquid crystal composition defined in claim 3.

9. A liquid crystal display device comprising a liquid crystal composition defined in claim 4.

10. A liquid crystal display device comprising a liquid crystal composition defined in claim 5.

* * * * *